(12) United States Patent
Takamura et al.

(10) Patent No.: US 7,875,825 B2
(45) Date of Patent: Jan. 25, 2011

(54) PLASMA GENERATING EQUIPMENT

(75) Inventors: Yuzuru Takamura, Ishikawa (JP); Akiko Iiduka, Hitachinaka (JP); Eiichi Tamiya, Kanazawa (JP)

(73) Assignee: Japan Advanced Institute of Science and Technology, Ishikawa (JP)

( * ) Notice: Subject to any disclaimer, the term of this patent is extended or adjusted under 35 U.S.C. 154(b) by 1129 days.

(21) Appl. No.: 10/593,771

(22) PCT Filed: Mar. 25, 2005

(86) PCT No.: PCT/JP2005/005471
§ 371 (c)(1),
(2), (4) Date: Sep. 22, 2006

(87) PCT Pub. No.: WO2005/093394
PCT Pub. Date: Oct. 6, 2005

(65) Prior Publication Data
US 2007/0164003 A1 Jul. 19, 2007

(30) Foreign Application Priority Data
Mar. 25, 2004 (JP) ............................. 2004-127380
Aug. 31, 2004 (JP) ............................. 2004-253664

(51) Int. Cl.
*B23K 9/02* (2006.01)
*G01J 3/30* (2006.01)
(52) U.S. Cl. .................................... 219/121.5; 356/311
(58) Field of Classification Search .................... 219/121.36–121.59; 356/311–334; 435/7.2, 435/287.1–288.7
See application file for complete search history.

(56) References Cited

U.S. PATENT DOCUMENTS
4,302,313 A * 11/1981 Columbus .................... 204/409

(Continued)

FOREIGN PATENT DOCUMENTS
JP 10-300671 A 11/1998

(Continued)

OTHER PUBLICATIONS

Jan C. T. Eijkel et al.; A Molecular Emission Detector on a Chip Employing a Direct Current Microplasma; Analytical Chemistry, vol. 71, No. 14, Jul. 15, 1999, pp. 2600-2606.

(Continued)

*Primary Examiner*—Sang Y Paik
(74) *Attorney, Agent, or Firm*—Birch, Stewart, Kolasch & Birch, LLP

(57) ABSTRACT

A method for generating plasma and a method for elemental analysis, each comprising the steps of providing a narrow portion in a flow channel made of an insulation material, the narrow portion having a cross-sectional area markedly smaller than a cross-sectional area of the flow channel; filling the flow channel and the narrow portion with a conductive liquid, and thereafter applying an electric field to the narrow portion, to conduct the electric field through the narrow portion, thereby generating plasma at the narrow portion. An apparatus for generating plasma, the apparatus for generating plasma comprising a narrow portion in a flow channel made of an insulation material, the narrow portion having a cross-sectional area markedly smaller than a cross-sectional area of the flow channel; and a means of applying an electric field to the narrow portion to conduct the electric field through the narrow portion; and an apparatus for emission spectroscopic analysis comprising the apparatus for generating plasma as defined above.

16 Claims, 10 Drawing Sheets

U.S. PATENT DOCUMENTS

| | | |
|---|---|---|
| 6,184,517 B1 | 2/2001 | Sawada et al. |
| 6,381,014 B1 * | 4/2002 | Platzer et al. ............... 356/316 |
| 6,686,998 B2 * | 2/2004 | Gianchandani et al. ..... 356/316 |
| 6,734,964 B1 * | 5/2004 | Duan et al. ................. 356/316 |
| 7,018,830 B2 * | 3/2006 | Wilding et al. ........... 435/287.1 |

FOREIGN PATENT DOCUMENTS

| | | |
|---|---|---|
| JP | 2002-257785 A | 9/2002 |
| JP | 3616088 B1 | 11/2004 |

OTHER PUBLICATIONS

Renato Guchardi et al.; Capacitively coupled microplasma for on-column detection of chromatographically separated inorganic gases by optical emission spectrometry, Journal of Chromatography A, 1033 (2004), pp. 333-338.

J. Hopwood et al.; A microfabricated atmospheric-pressure microplasma source operating in air; Journal of Physics D: Applied Physics 38 (2005), pp. 1698-1703.

Kazuhisa Azumi et al.; Light Emission Spectroscopy from Metal Electrodes during Electrolysis; Electrochemistry, 67(4), 1999, pp. 349-354.

* cited by examiner

[Figure 1]
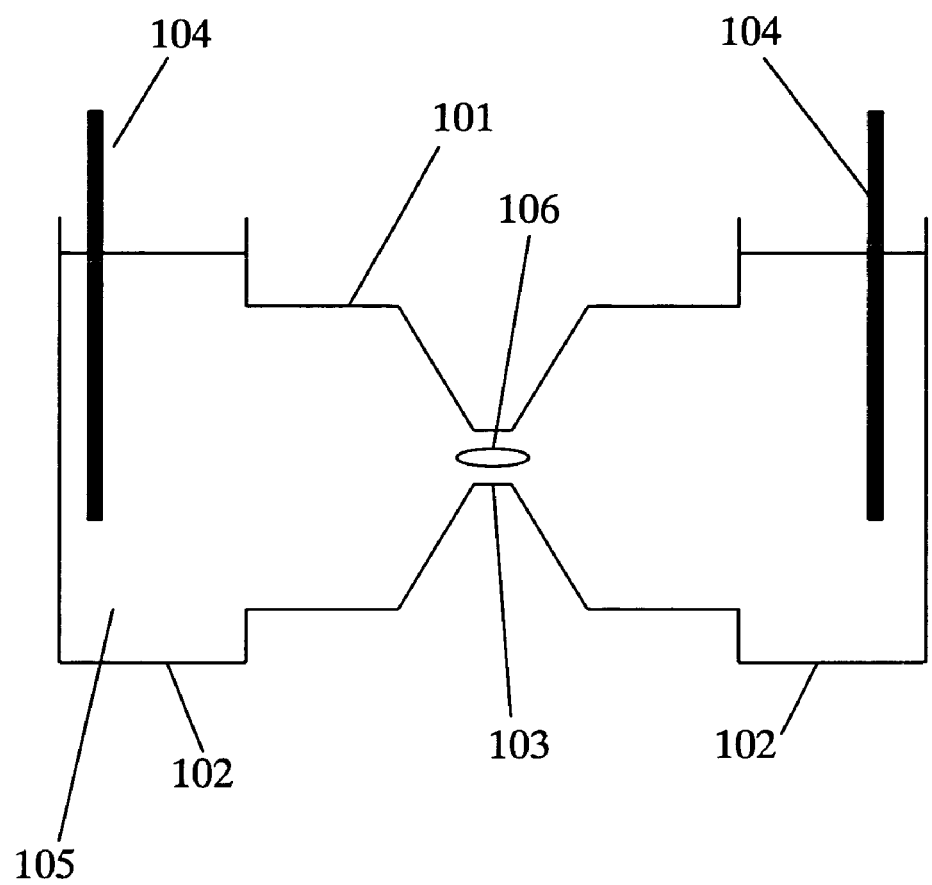

[Figure 2]
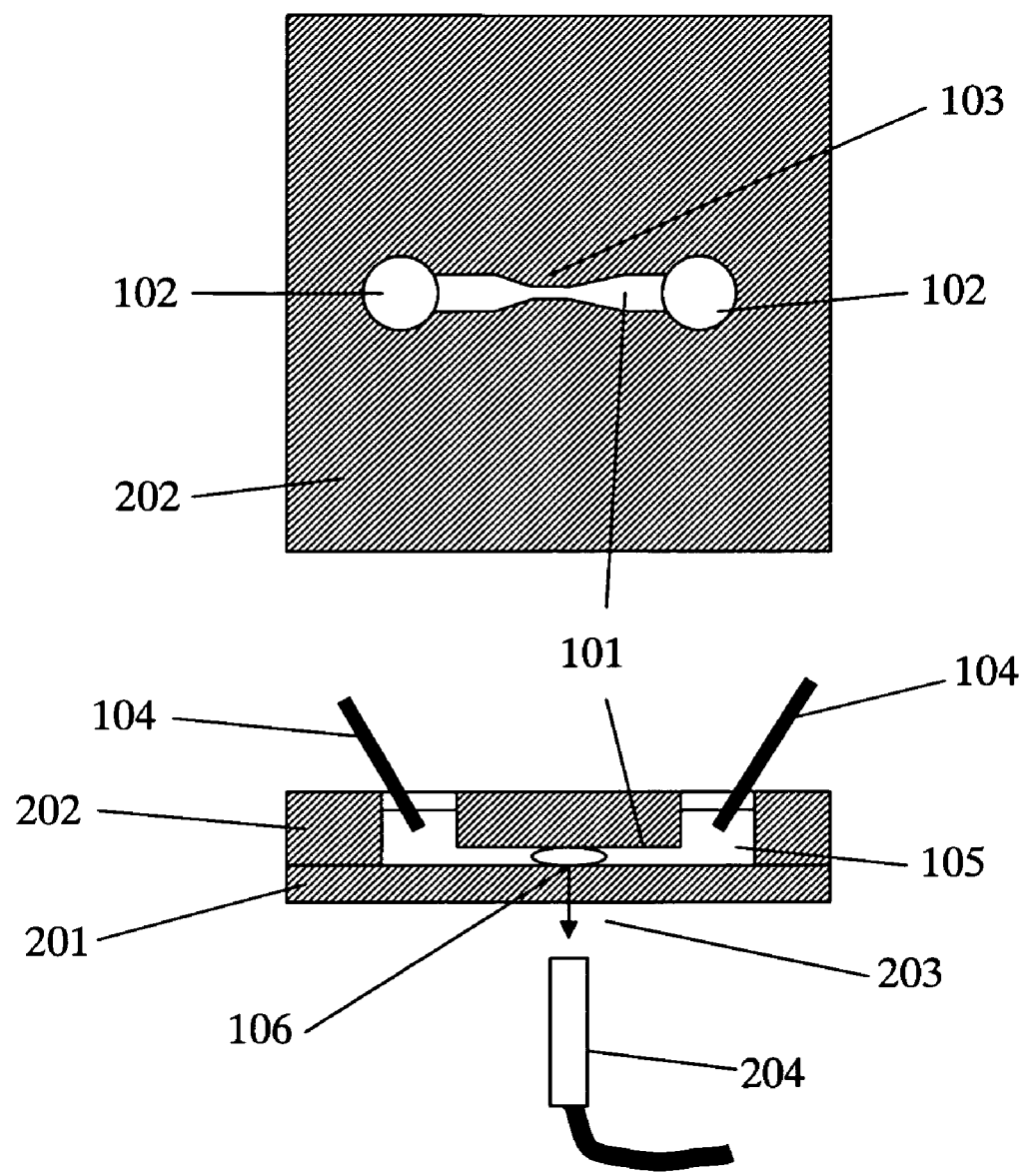

[Figure 3]
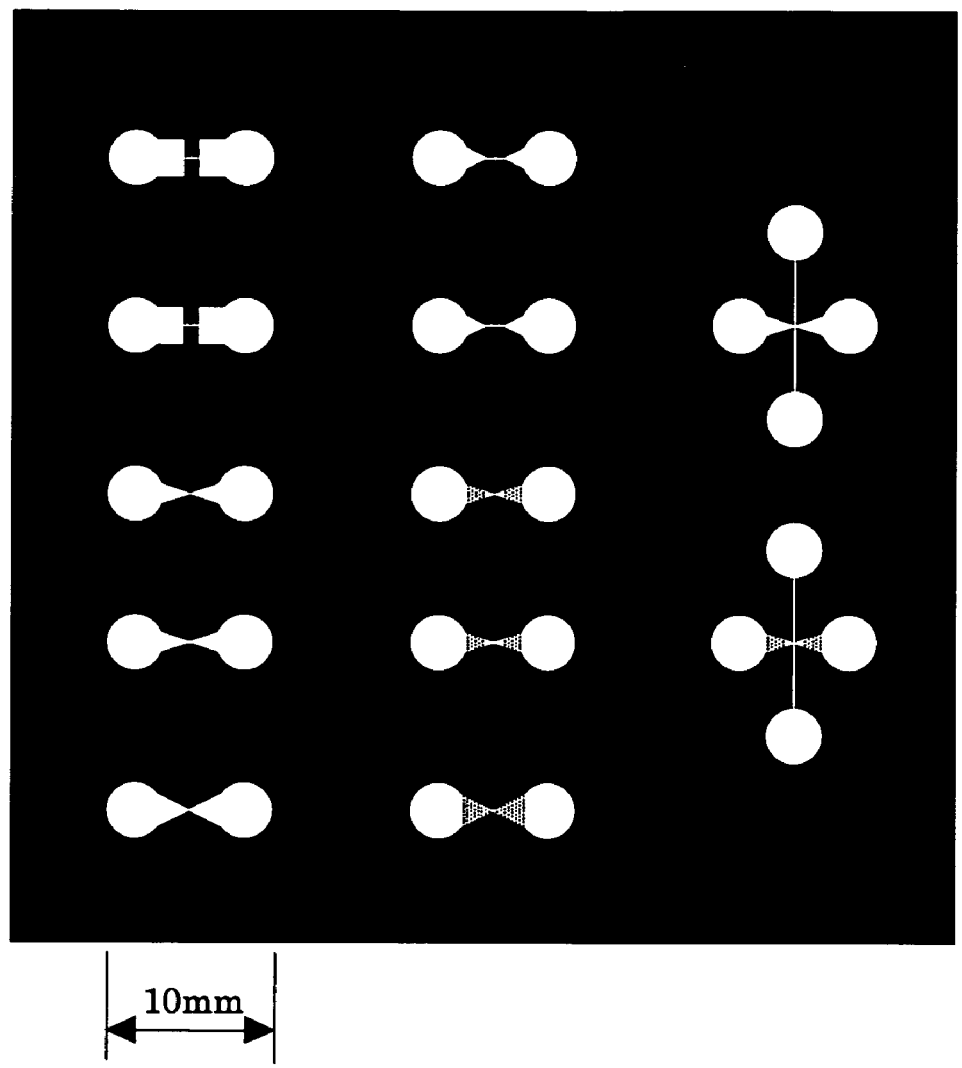

[Figure 4]
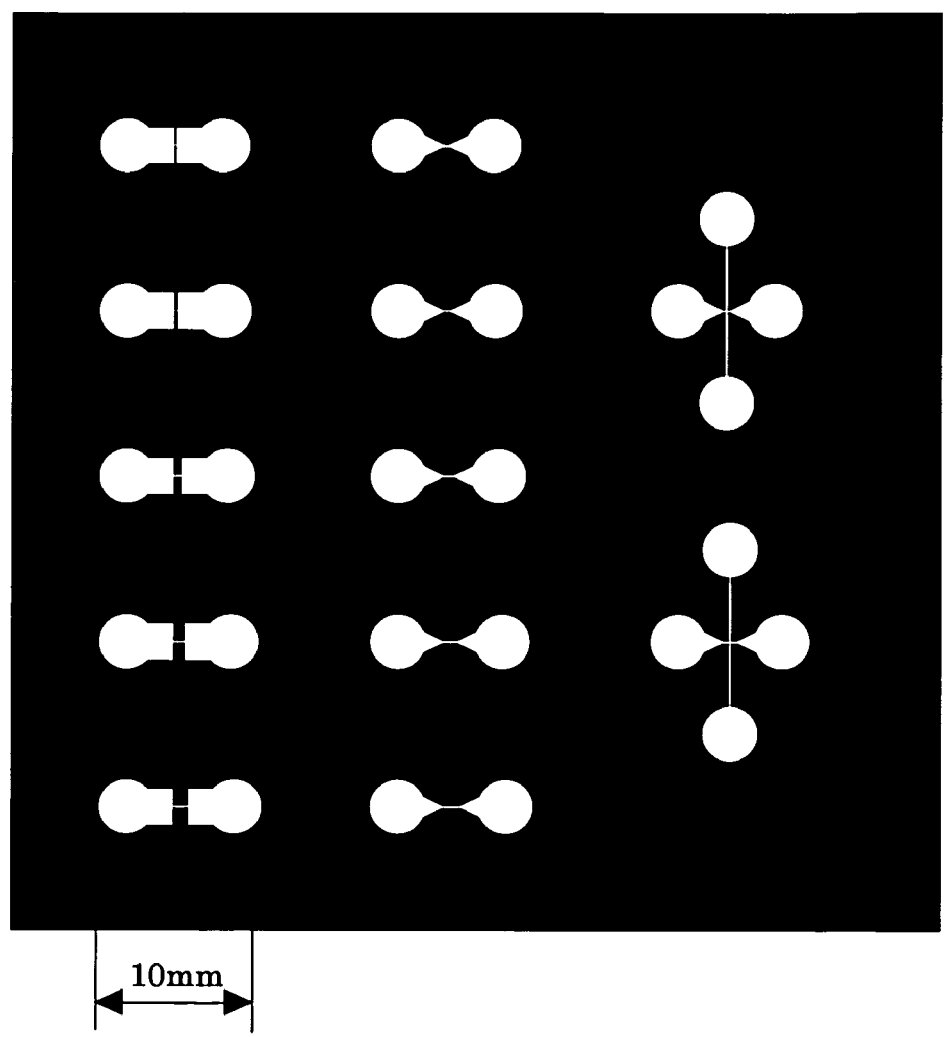

[Figure 5]
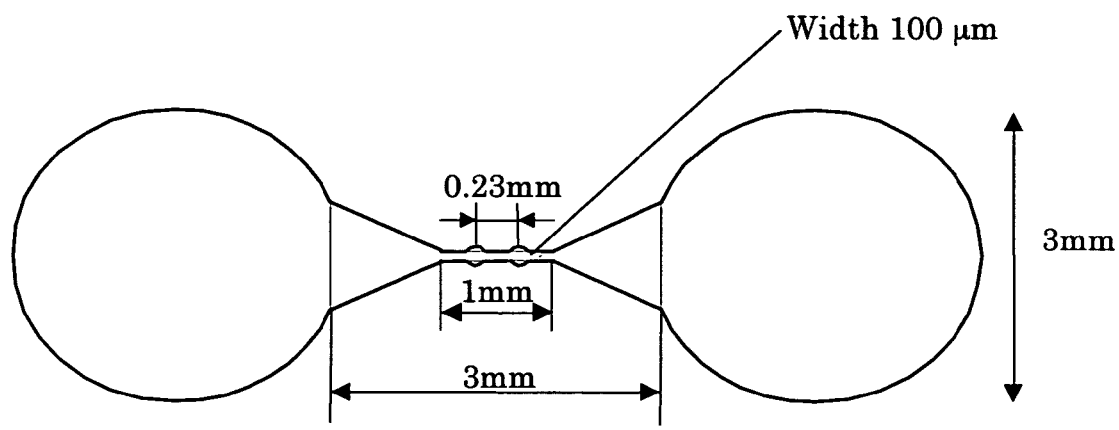
[Figure 6]
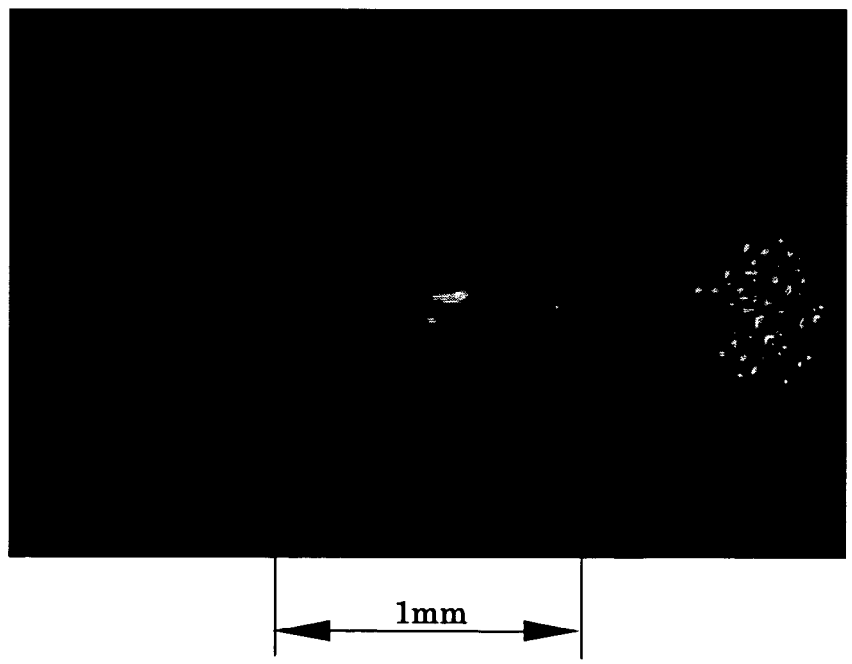

[Figure 7]
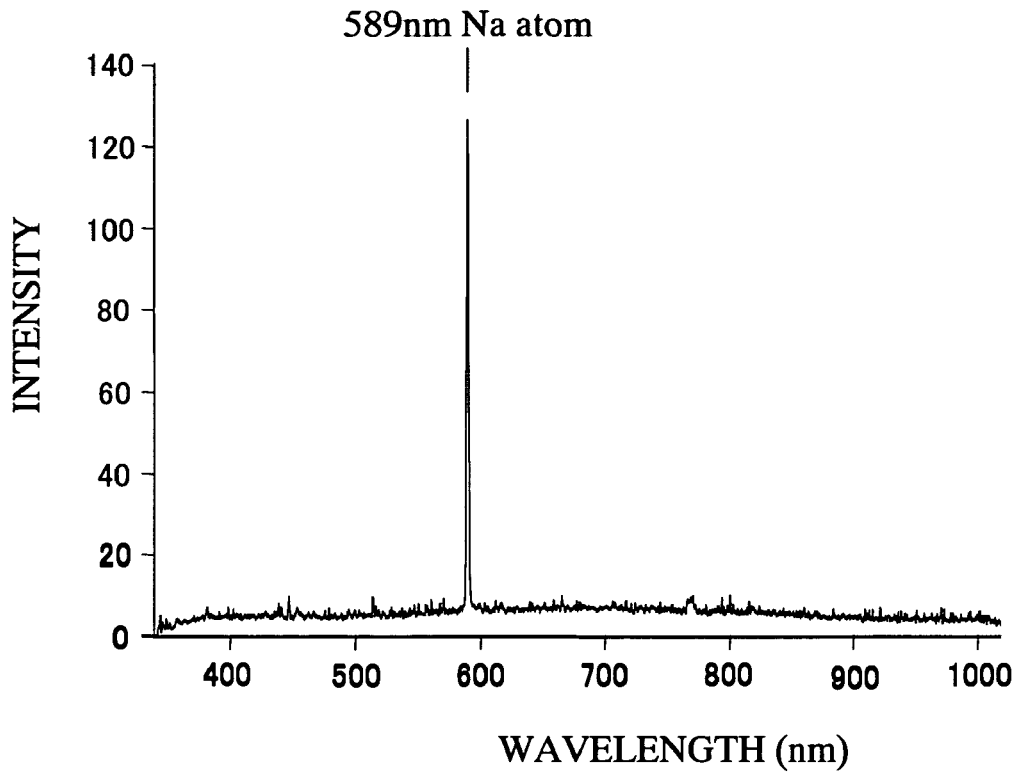
[Figure 8]
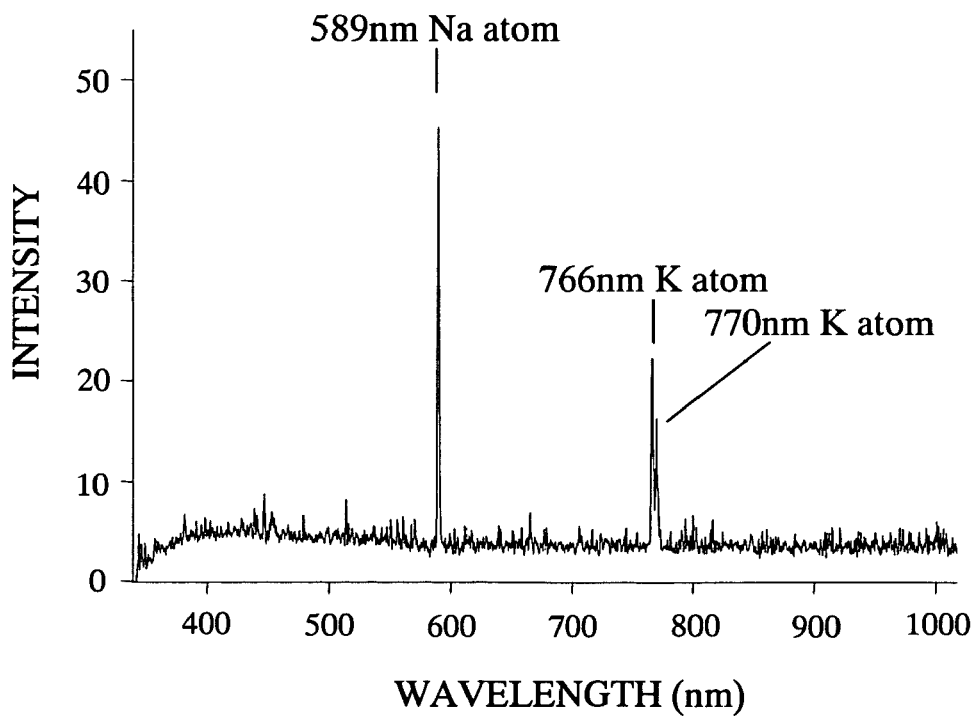

[Figure 9]
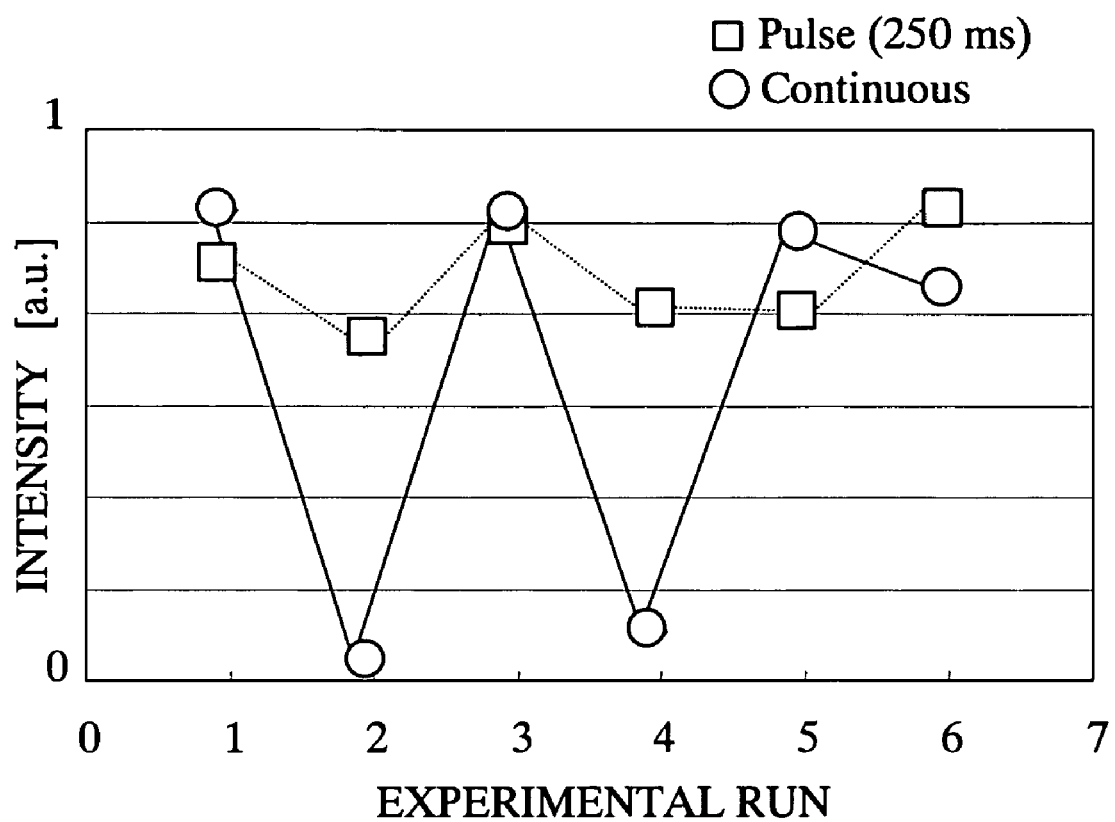

[Figure 10]
(a)
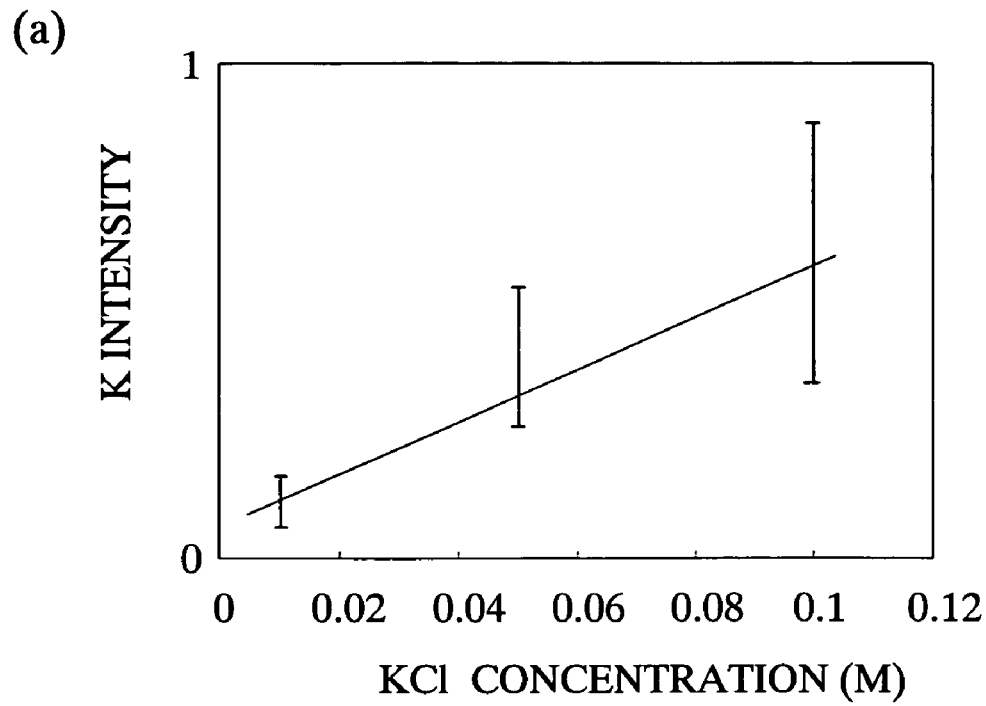
(b)
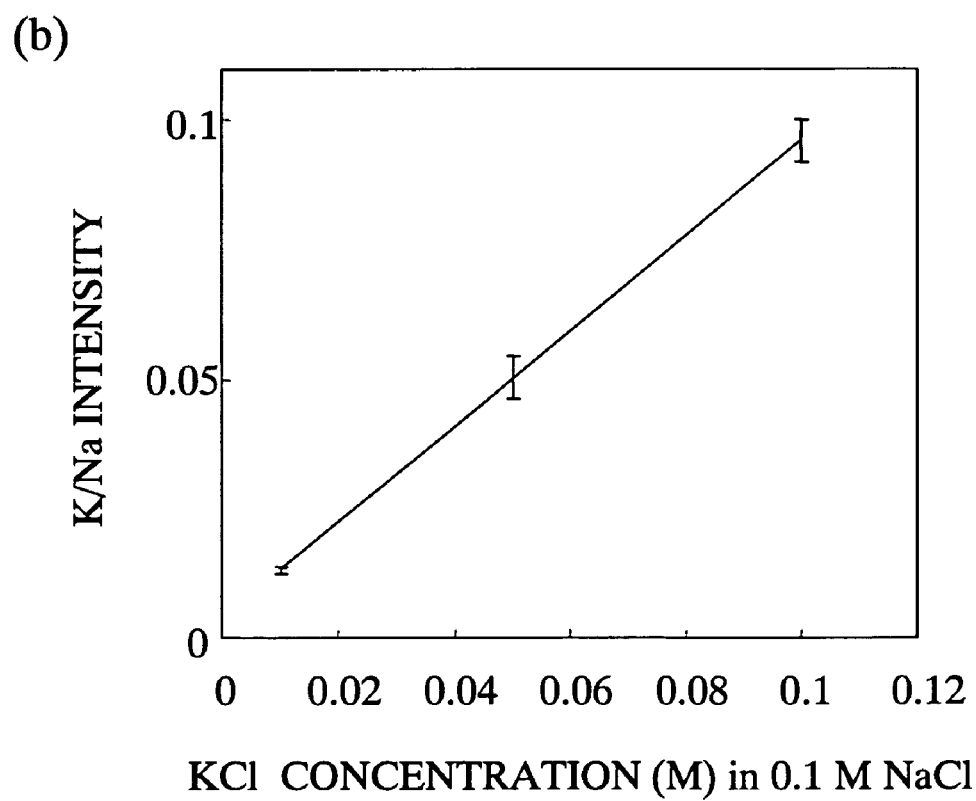

[Figure 11]
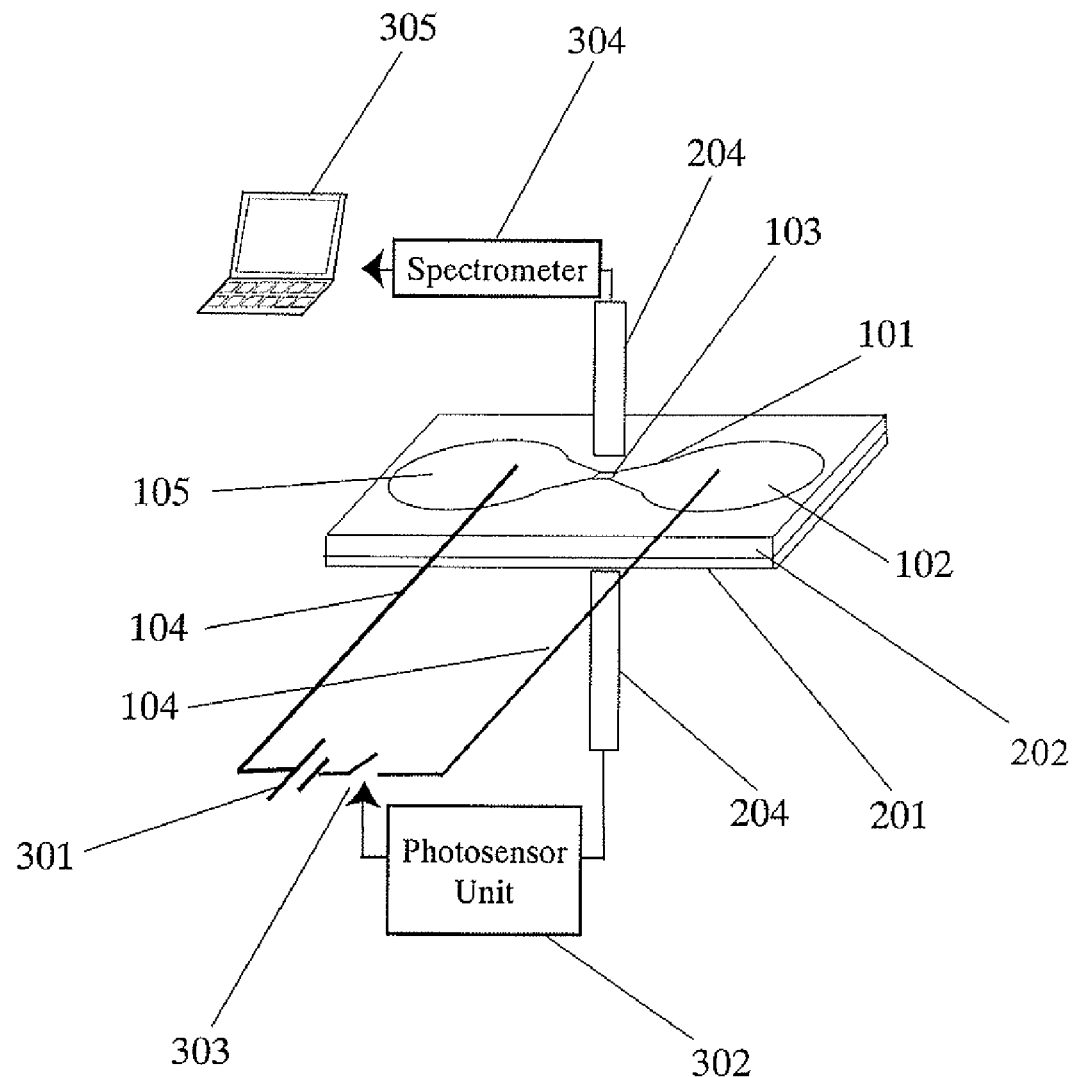

[Figure 12]
(a)
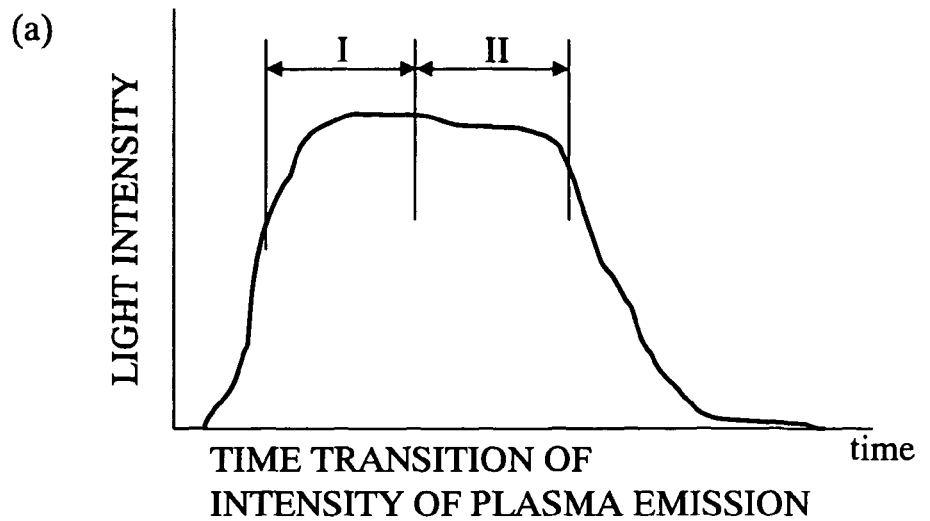
(b)
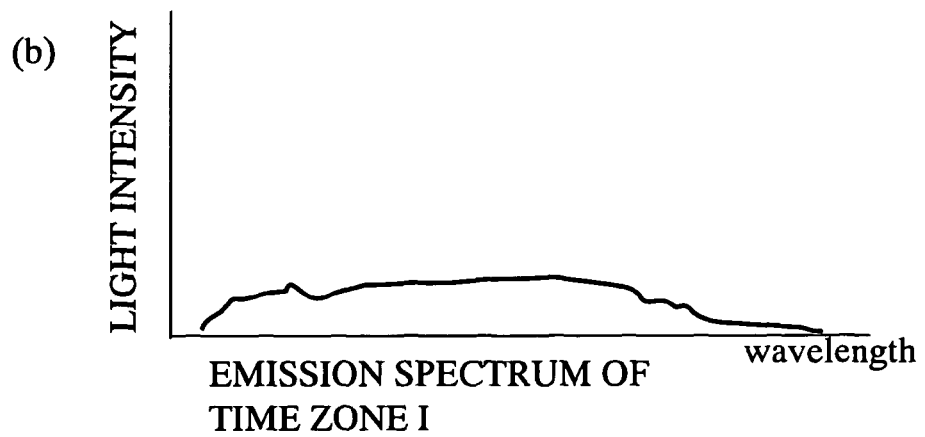
(c)
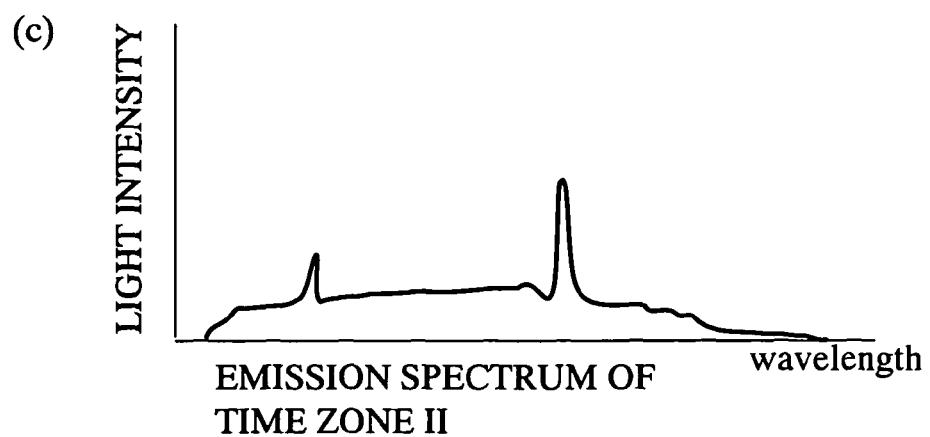

PLASMA GENERATING EQUIPMENT

TECHNICAL FIELD

The present invention relates to an apparatus for generating plasma. More specifically, the present invention relates to a method for generating plasma, a method for emission spectroscopic analysis, and an apparatus for generating plasma, and an apparatus for emission spectroscopic analysis in which the apparatus for generating plasma is used, for identification and quantification of elements contained in a solution according to emission spectra from the elements contained in a solution. The method for generating plasma and the apparatus for generating plasma of the present invention can be suitably used in the field of microfluid mechanics or the fields called μTAS (micro total analysis systems) or lab-on-a-chip. According to the present invention, a part of an especially necessary function and structure can be integrated on a single plate-like chip. The apparatus for generating plasma of the present invention may be carried out with only a trace amount of necessary samples and has the features of portability, immediacy, easy maintenance, low costs, or the like.

BACKGROUND ART

An inductively coupled plasma optical emission spectrometer (ICP optical emission spectrometer) has been widely used in analysis of elements contained in a solution. Inductively coupled plasma has the advantages of not necessitating the use of electrodes exposed to plasma during the generation and having a smaller amount of contamination of impurities from the electrodes. On the other hand, apparatus for generating plasma other than the ICP optical emission spectrometer are subjected to contamination of impurities from electrodes or the like, so that the apparatus are not suitable for high-sensitivity elemental analysis.

In recent years, a microfluidic device, and a research field called μTAS, or lab-on-a-chip have been rapidly developed, in which a small flow channel, a reaction vessel, and an analytical device are built on a wafer by applying semiconductor processes, to try accomplishing a set of chemical experiments necessary for a blood test or the like on one chip. In this field, in order to perform high-sensitivity elemental analysis, a method of performing elemental analysis comprising the steps of generating microplasma, and introducing a nebulized solution therein has been developed.

As the microplasma, those obtained by miniaturizing a direct current plasma, a capacitively coupled plasma, an inductively coupled plasma, or the like has been known. For example, a microchemical analysis system for performing emission spectroscopic analysis (see, for example, Patent Publication 1) or the like has been proposed.

However, in order to generate stable plasma by these methods for generating plasma, there are some disadvantages in these methods that during the generation of plasma, a gas pressure reduction is necessitated, that a gas that can easily maintain plasma such as helium is used, or that radio frequency is necessitated. In addition, in order to prevent damages caused by heat to the apparatus while maintaining plasma, there are not only a disadvantage that a certain level of a gas flow rate is necessary so that its usability is poor in that a large tank is necessary or the like, but also a disadvantage that high electric power is necessitated for the generation of plasma. Furthermore, in order to introduce a sample into plasma, it is necessary to gasify the sample, so that a nebulizer is necessitated in order to spray the sample in a nebulized state. Since it is difficult to miniaturize the nebulizer, a considerable amount of flow rate of nebulized gas is necessitated. Therefore, when the nebulized gas is introduced into plasma, the nebulized gas perturbs the plasma. In order to tolerate the perturbation, the size of the plasma is necessitated to have a certain degree of largeness. Accordingly, it has been difficult to miniaturize an emission spectrometer in which a nebulizer is used, and no emission spectrometer having favorable performance has conventionally been obtained.

As an alternative method for generating plasma, there has been reported a method comprising inserting electrodes into a solution and conducting a direct current to the solution, thereby generating plasma (see, for example, Non-Patent Publication 1).

An advantage of this method is that a nebulizer is not necessitated because plasma is generated in a solution and the vaporization of the solution serves as a function of gasifying the sample. However, on the principle of the generation of plasma, the efficiencies for generating and maintaining plasma are higher on an interface between the surface of a solid electrode and a gas than those on a gas-liquid interface, in a solution, or in a gas. Therefore, there are some defects in the conventional method that since a solid electrode always contacts with the plasma, impurities contained in the solid electrode are vaporized, thereby making it difficult to avoid contamination of the impurities.

Patent Publication 1: Japanese Patent Laid-Open No. 2002-257785

Non-Patent Publication 1: Kazuhisa AZUMI, Masahiro SEO, and

Tadahiko MIZUNO; "Light Emission Spectroscopy from Various Metal Electrodes During Electrolysis), *Electrochemistry*, 67(4),1999, 349-354, internet <URL: 1111641682281_0.html>

DISCLOSURE OF INVENTION

Problems to be Solved by the Invention

The present invention has been accomplished in view of the conventional techniques mentioned above. An object of the present invention is to provide a method for generating plasma capable of simply generating plasma with a smaller amount of contamination of impurities when emission spectrometry of an element contained in a conductive liquid is performed; a method for elemental analysis capable of readily performing elemental analysis using the generated plasma; an apparatus for generating plasma; and an apparatus for emission spectroscopic analysis in which the apparatus for generating plasma is used.

Means to Solve the Problems

Specifically, the gist of the present invention relates to:
(1) a method for generating plasma comprising the steps of providing a narrow portion in a flow channel made of an insulation material, the narrow portion having a cross-sectional area markedly smaller than a cross-sectional area of the flow channel; filling the flow channel and the narrow portion with a conductive liquid, and thereafter applying an electric field to the narrow portion, to conduct the electric field through the above-mentioned narrow portion, thereby generating plasma at the above-mentioned narrow portion;
(2) a method for elemental analysis comprising the steps of providing a narrow portion in a flow channel made of an insulation material, the narrow portion having a cross-sectional area markedly smaller than a cross-sectional area of the flow channel; filling the flow channel and the narrow portion with a conductive liquid for identification or quantification of elements, and thereafter applying an electric field to the narrow portion to conduct the electric field through the above-mentioned narrow portion, thereby generating plasma at the above-mentioned narrow portion; and subjecting light from the generated plasma to spectroscopy;

(3) an apparatus for generating plasma in a conductive liquid, the apparatus comprising a narrow portion and arranged in a flow channel made of an insulation material, the narrow portion having a cross-sectional area markedly smaller than a cross-sectional area of the flow channel; and a means of applying an electric field to the narrow portion to conduct the electric field through the above narrow portion; and (4) an apparatus for emission spectroscopic analysis comprising the above apparatus for generating plasma.

Effects of the Invention

According to the present invention, when elements contained in a conductive liquid are subjected to emission spectroscopy, an effect that plasma can be simply generated with a smaller amount of contamination of impurities is exhibited.

In addition, the apparatus for generating plasma and apparatus for emission spectroscopic analysis of the present invention realize miniaturization of the apparatus, drastic reduction in gas consumption and power consumption, and cost reduction of the apparatus, while maintaining the same level of performance as the ICP optical emission spectroscopy. Therefore, the apparatus for generating plasma and apparatus for emission spectroscopic analysis of the present invention can be miniaturized to a size approximately that can be held on the palm of a hand, even when the apparatus includes a battery (cell) and a spectrometer, as a substitute of conventional, large ICP optical emission spectrometers which consume a large amount of gas and electric power.

Recently, with the worsening of the environment, soil and water pollution, and food pollution have been issues of problems. The apparatus for generating plasma and the apparatus for emission spectroscopic analysis of the present invention are expected to be utilized as a tool capable of conveniently analyzing a polluted situation on the spot.

In addition, in the microfluid technology such as μTAS and lab-on-a-chip, a high-sensitivity microanalysis of a sample has been earnestly desired, and the present invention is also expected to give a solution thereto. Furthermore, since the present invention realizes simple generation of plasma without corrosion of electrodes, it is expected to be utilized in various applications of microplasma.

BRIEF DESCRIPTION OF THE DRAWINGS

[FIG. 1] A schematic explanatory view of the method for generating plasma of the present invention.

[FIG. 2] A schematic explanatory view showing one embodiment of the apparatus for generating plasma of the present invention.

[FIG. 3] A schematic plan view of a flow channel pattern 1 in the apparatus for generating plasma shown in FIG. 2 of the present invention.

[FIG. 4] A schematic plan view of a flow channel pattern 2 in the apparatus for generating plasma shown in FIG. 2 of the present invention.

[FIG. 5] A schematic plan view showing one embodiment of a flow channel pattern in which plasma generates stably in the present invention.

[FIG. 6] A photograph showing a state where a microplasma is generated in the present invention.

[FIG. 7] A graph showing an emission spectrum when a phosphate buffer is subjected to elemental analysis using the apparatus for generating plasma of the present invention.

[FIG. 8] A graph showing an emission spectrum when an aqueous potassium chloride is subjected to elemental analysis using the apparatus for generating plasma of the present invention.

[FIG. 9] A graph showing the measurement results for the stability of the plasma emission in the case where plasma is continuously generated and in the case where plasma having a pulse width is generated, according to the present invention.

[FIG. 10] Graphs showing calibration curves and variance when plasma is generated according to the present invention.

[FIG. 11] A schematic explanatory view showing one embodiment of the apparatus for emission spectroscopic analysis in which the apparatus for generating plasma of the present invention is used.

[FIG. 12] Graphs showing a time transition of the intensity of plasma emission, and a relationship between the wavelength and the light intensity of the emission spectrum when plasma is generated according to the present invention.

EXPLANATION OF NUMERALS 101 flow channel
102 solution reservoir
103 narrow portion
104 electrode
105 conductive liquid
106 plasma
201 quartz glass
202 chip
203 light from plasma
204 optical fiber
301 power supply
302 photosensor unit
303 switch
304 spectrometer
305 computer

BEST MODE FOR CARRYING OUT THE INVENTION

According to the method for generating plasma of the present invention, by providing a narrow portion in a flow channel made of an insulation material, the narrow portion having a cross-sectional area markedly smaller than a cross-sectional area of the flow channel; filling the flow channel and the narrow portion with a conductive liquid, and thereafter applying an electric field to the narrow portion to conduct the electric field through the above-mentioned narrow portion, plasma can be generated at the above-mentioned narrow portion.

In addition, according to the elemental analysis method of the present invention, elemental analysis can be performed by providing a narrow portion in a flow channel made of an insulation material, the narrow portion having a cross-sectional area markedly smaller than a cross-sectional area of the flow channel; filling the flow channel and the narrow portion with a conductive liquid for identification or quantification of elements, and thereafter applying an electric field to the narrow portion to conduct the electric field through the above-mentioned narrow portion, thereby generating plasma at the above-mentioned narrow portion; and subjecting the light from the generated plasma to spectroscopy.

The flow channel made of an insulation material is formed by providing a microflow channel in an insulation material. The insulation material includes, for example, glass, olefin-based resins such as polyethylenes and polypropylenes; silicone such as polydimethyl siloxane; fluororesins, ceramics, and the like. The present invention is not limited only to those exemplified above.

The flow channel can be formed, for example, on a plate-like chip or a plate, each made of an insulation material, using a lithographic technique.

In addition, when a molded article having a shape which is detachably arranged in the flow channel is constructed as a cartridge by, for example, an injection molding method or the like, capable of mass production, the narrow portion can be properly exchanged with a fresh one after use. Especially, when an element contained in a conductive liquid is analyzed with high sensitivity, it is important to eliminate contamination of the devices upon the use of the conductive liquid used in the previous elemental analysis. When a container containing the conductive liquid, or a narrow portion and a flow channel are detachably constructed with a resin molded article for exchangeable, inexpensive consumables, the occurrence of the disadvantage caused by contamination in system can be prevented by exchanging the consumables with fresh ones, thereby making it suitable for high-sensitive elemental analysis. As the above-mentioned resin, for example, a resin having thermoplasticity and excellent ultraviolet transmittance can be suitably used.

In a flow channel, a narrow portion having a cross-sectional area markedly smaller than a cross-sectional area of the flow channel is provided. Here, the cross-sectional area of the flow channel or the narrow portion means a cross-sectional area of a cross section to the flow channel, in other words, a cross-sectional area of the flow channel or of the narrow portion in a direction perpendicular to the direction of the electric field in the flow channel or the narrow portion.

The length in a width direction of the flow channel to the narrow portion is preferably from 2 μm to 30 mm, more preferably from 300 μm to 5 mm, and even more preferably from 500 μm to 1 mm, from the viewpoint of having a volume of a solution necessary for measurement as small as possible, and conducting the conductive liquid and/or the electric field to the narrow portion with sufficient ease, and also securing a cross-sectional area of a flow channel sufficiently wide, as compared to the cross-sectional area of the narrow portion.

The above-mentioned width means a size of the flow channel in the cross section of the flow channel. Especially, when a flow channel 101 and a narrow portion 103 are constructed to be planar, the flow channel and the narrow portion being as shown in FIG. 2, the width further means a size of the flow channel in the direction intersecting the plane with the cross section of the flow channel.

In addition, as shown in FIG. 2, especially when the flow channel 101 and the narrow portion 103 are constructed to be planar, the length in the thickness direction of the flow channel, which is a size of the flow channel in the direction perpendicular to the above-mentioned width in the cross section of the flow channel, is preferably from 0.5 μm to 1 mm, more preferably from 10 μm to 300 μm, and even more preferably from 50 μm to 200 μm, from the viewpoint having a volume of a solution necessary for measurement as small as possible, conducting the conductive liquid and the electric field to the narrow portion with sufficient ease, and also securing a cross-sectional area of a flow channel sufficiently wide, as compared to the cross-sectional area of the narrow portion. The above-mentioned cross section of the flow channel is a cross section of the flow channel in a plane perpendicular to the direction of the electric field in the flow channel.

The length of the narrow portion in the direction of the electric field is preferably from 2 μm to 3 mm, and more preferably from 50 μm to 1 mm, in order to easily generate plasma, stabilize the location of the generation of plasma, and obtain a sufficient amount of emission from the plasma. Each of the length in the thickness direction and the length in the width direction of the narrow portion is preferably from 0.5 μm to 1 mm, more preferably from 10 μm to 300 μm, and even more preferably from 50 μm to 200 μm, from the viewpoint of making the size of the cross-sectional area of the narrow portion sufficiently smaller than that of the flow channel, easily generating plasma, stabilizing the location of generation of plasma, and obtaining a sufficient amount of emission from the plasma.

The above-mentioned length in the width direction means a size of the flow channel in the cross section of the narrow portion perpendicular to the above-mentioned length in the direction of the electric field. As shown in FIG. 2, when the flow channel 101 and the narrow portion 103 are constructed to be planar, the length in the width direction further means a size of the flow channel in the direction intersecting the plane with the above-mentioned cross section of the narrow portion. Similarly, the above-mentioned length in the thickness direction means a size of the flow channel in the direction perpendicular to the above-mentioned length in the width direction in the above-mentioned cross section of the narrow portion.

The cross-sectional area of the narrow portion is markedly smaller than that of the flow channel. The value of the ratio of the cross-sectional area of the flow channel to that of the narrow portion (cross-sectional area of the flow channel/cross-sectional area of the narrow portion) is, for example, preferably 3 or more, more preferably 10 or more, even more preferably 30 or more, and even more preferably 100 or more, as shown in FIG. 5, from the viewpoint of efficiently generating plasma. The upper limit of the above-mentioned value of the ratio of the cross-sectional area of the flow channel to that of the narrow portion (cross-sectional area of the flow channel/cross-sectional area of the narrow portion) is not particularly limited, and the present invention is not limited by the upper limit. Usually, the upper limit is preferably 10,000 or less, more preferably 8,000 or less, and even more preferably 5,000 or less.

The shape of the cross section of the flow channel and the shape of the cross section of the narrow portion are not particularly limited. Examples of the shapes of the cross sections thereof include rectangular, square, triangular, circular, elliptic shapes, and the like.

The position of the narrow portion provided in the flow channel is not particularly limited. For example, the narrow portion can be provided near the center of the flow channel. The narrow portion can be formed by providing a portion in which the cross-sectional area of the flow channel is dramatically reduced. It is desired in a connected portion of the flow channel and the narrow portion that the flow channel and the narrow portion are connected at an angle of from 10° to 90°, and preferably from 10° to 80° with respect to the axial direction of the flow channel, from the viewpoint of smoothly introducing the conductive liquid without admixing bubbles in the solution, and from the viewpoint of appropriately concentrating an electric field.

The flow channel and the narrow portion are filled with a conductive liquid. As the conductive liquid, a liquid sample to be analyzed is used. An electrolyte used in the conductive liquid includes, for example, nitric acid, acetic acid, hydrochloric acid, and the like. Among them, nitric acid is preferable from the viewpoint of being less likely to cause troubles in the analysis. It is preferable that the sample is an electrolyte containing an element that does not hinder analysis such as nitric acid, and imparts conductivity.

Next, an electric field is applied to the narrow portion to conduct an electric field through the above-mentioned narrow portion, for example, by a method comprising applying an electric field along a narrow portion. By the application of the electric field, bubbles are generated in the above-mentioned narrow portion, whereby plasma can be generated in the formed bubbles.

Electric current can be conducted from, for example, electrodes inserted into the flow channel. In addition, an induced electric current can also be utilized as an electric current. As an electrode, a solid electrode can be used, and a pair of electrodes can be arranged in the flow channel so that the narrow portion is sandwiched. When the electrodes are arranged as described above and an electric field is applied between both the electrodes, the conductive liquid is heated, whereby bubbles can be generated.

The voltage and the electric current cannot be unconditionally determined, because they may differ depending upon the length of the flow channel, the kinds of the electrolytic solutions, and the like. Usually, it is desired that the voltage is preferably from 30 to 5000 V, and more preferably from 100 to 1500 V; and the electric current is preferably from 0.1 to 1,000 mA, and more preferably from 2 to 100 mA.

In addition, an intensity of the electric field in the narrow portion differs depending upon the length of the flow channel, the kinds of the electrolytic solution, and the like in the same manner as above, and is further subject to change together with the generation of bubbles and plasma. Before the generation of the bubbles, the intensity is preferably from 0.01 to 100 MV/m, and more preferably from 1 to 10 MV/m, from the viewpoint of stably and quickly generating the bubbles and plasma, efficiently emitting light from constituent elements in the solution, and not giving damages that are more than necessary to the constituting materials of the flow channel and the narrow portion.

In the manner as described above, when an electric field is applied to the narrow portion, the electric field is concentrated to the narrow portion to boil the conductive liquid, thereby vaporizing the liquid to generate bubbles, at which time plasma is generated.

In the portion where the electrode is inserted into the conductive liquid, the electric field is sufficiently weak and the electric current density is low, so that plasma is not generated. The plasma generated in the bubbles does not directly contact with the electrode, and the conductive liquid itself, which has conductivity and is a subject to be measured, plays a role of an electrode which is contacted with plasma to give an electric field. Therefore, there is very little contamination by additional impurities caused by evaporation of the electrodes or the like. The elements contained in very small amounts in the conductive liquid can be very simply subjected to elemental analysis with high sensitivity, from quantification of the emission spectrum of this plasma.

In addition, since the size of the flow channel and the narrow portion is very small, the side wall of the flow channel in proximity to the plasma is powerfully cooled from the surroundings, and contamination of the impurities from the side wall of the flow channel is also suppressed. When the side wall of the flow channel is sufficiently cooled, the contamination of the impurities from the side wall of the flow channel can further be suppressed by covering the surface of the side wall with the conductive liquid.

Here, after an electric field for generating plasma is applied in the form of a pulse, in other words, an electric field is applied, the application of the electric field is forcibly stopped in a short time to control the application time period per single application of electric field to a short period of time, whereby the size and the state of the generated plasma can be controlled, so that reproducibility of the state of the generation of plasma and precision of the elemental analysis can be increased. The above-mentioned short period of time is usually from 1 µs to 500 ms, and preferably from 20 µs to 5 ms. The conditions necessary for the generation of plasma such as electric field and the state of generation of plasma depend upon the electroconductivity of the conductive liquid. However, the conditions such as voltage for generating plasma in the most stable manner and the condition of atomic emission can be maintained at given levels by previously adding to a conductive liquid a given electrolyte which is irrelevant to analysis of the conductive liquid, thereby adjusting the electroconductivity of the conductive liquid.

In addition, in the plasma emission spectrum, more precise quantification of elements can be performed by comparing the intensity of the emission from the added electrolyte with the intensity of the emission from the elements to be determined which are contained in the conductive liquid. Even higher precise quantification of elements can be performed by repeating quantification and accumulating the results, thereby extending a total time for the generation of plasma. At this time, when plasma is generated while the conductive liquid in the flow channel and the narrow portion is allowed to migrate, a fresh conductive liquid can always be present in the narrow portion, so that the precision can be more increased.

The apparatus for generating plasma of the present invention is an apparatus for generating plasma in a conductive liquid, comprising a narrow portion and arranged in a flow channel made of an insulation material, the narrow portion having a cross-sectional area markedly smaller than a cross-sectional area of the flow channel; and a means for applying an electric field to the narrow portion to conduct the electric field through the narrow portion. Also, the apparatus for emission spectroscopic analysis of the present invention comprises the above-mentioned apparatus for generating plasma. The apparatus for generating plasma and the apparatus for emission spectroscopic analysis comprising the apparatus for generating plasma of the present invention will be explained in detail on the basis of the following Examples.

By using the apparatus for generating plasma and the apparatus for emission spectroscopic analysis comprising the apparatus for generating plasma of the present invention, the amount of contamination of impurities can be reduced, so that the elements can be easily subjected to, for example, qualitative analysis and quantitative analysis.

When the plasma is generated in the form of a pulse, the timing for incorporating the light signal and the time interval are controlled by synchronizing them with the timing of the pulse-like plasma. Therefore, in the elemental analysis, the signal components are increased, and noise components and variance components are reduced, whereby precision and sensitivity of the analysis can be improved.

Furthermore, the plasma generated according to the present invention can be regarded as the one in which a portion for generating plasma is improved in the ICP emission spectroscopy, which is currently the mainstream in elemental analysis of liquids. By applying the present invention to the method for generating plasma of the ICP mass spectroscopy, which is also a method for elemental analysis of liquids of which detection method is different, the mass spectrometry using the plasma obtained by the present invention can also be performed.

Also, the plasma generated according to the present invention is a kind of microplasma, so that the plasma can also be utilized in applications for other microplasmas such as light sources, chemical reaction, processing of substances, or decomposition of substances.

Further, the apparatus for generating plasma of the present invention can be regarded as a new element technology of μTAS. By combining this apparatus with the existing element technology of μTAS, various systems incorporating a high-sensitive elemental analyzer can be considered. In addition, by combining the apparatus for emission spectroscopic analysis of the present invention with a liquid-feeding mechanism, a binary liquid mixing mechanism, a heating mechanism, or the like, a measurement system in which a pretreatment of removing an organic component from an organic substance sample and an adjustment processing such as adjustment of electroconductivity are incorporated can be constructed to be planar in one chip.

EXAMPLES

The present invention will be explained in further detail hereinbelow on the basis of Examples, without intending to limit the present invention only to the Examples.

Example 1

One embodiment of the method for generating plasma of the present invention is shown in FIG. 1. FIG. 1 shows a basic form for generating plasma according to the present invention.

The side wall of a flow channel 101 is formed with an insulation material. The flow channel 101 confines a conductive liquid 105, and at the same time determines a pathway for conducting electric current. Solution reservoirs 102 are connected to the flow channel 101. The conductive liquids 105 are stored individually in solution reservoirs 102, and introduced into the flow channel 101. A narrow portion 103 is connected to the flow channel 101, the narrow portion having a cross-sectional area smaller than the other portions (the flow channel 101 and the solution reservoirs 102). Therefore, at the narrow portion 103, electric current and the electric field are concentrated, so that the temperature at the narrow portion becomes higher than those at the other portions, whereby boiling and generation of plasma are likely to take place. The size of this narrow portion 103 and the shape of the flow channel 101 leading to the narrow portion 103 are important for stabilization of plasma.

As the material used in electrodes 104, a precious metal such as platinum, carbon or the like, which is less likely to cause corrosion by allowing electric current to flow therethrough is suitable.

It is necessary that the conductive liquid 105 contains an element that is subject to measurement and has conductivity. In order to impart conductivity to the conductive liquid 105, an electrolyte (supporting salt) is usually used, but a metal salt is not so suitable because the metal salt emits intensive light. Among the electrolytes, nitric acid is suitable because constituting elements of nitric acid are contained in the atmosphere as well as in water, and also has the property of melting metals well. The liquid temperature of the conductive liquid 105 is not particularly limited. It is desired that the liquid temperature is usually from 15° to 40° C. or so, and preferably from 20° to 25° C. or so.

When an electric field is applied between the electrodes 104, 104, the electric current and the electric field are generated in the narrow portion 103, so that bubbles are generated, and plasma 106 is generated in the formed bubbles. By subjecting light from the plasma 106 to spectroscopy, the elemental analysis of the conductive liquid 105 can be easily performed.

Example 2

One embodiment of the apparatus for generating plasma of the present invention is shown in FIG. 2. In FIG. 2, the upper figure is a schematic plan view showing one embodiment of the apparatus for generating plasma of the present invention. Here, the electrodes are omitted from the drawing. In FIG. 2, the lower figure is a schematic cross-sectional view in the central portion of the flow channel 101 of the apparatus for generating plasma shown in the above-mentioned upper figure. When the apparatus for generating plasma shown in FIG. 2 is used, the elemental analysis can be performed by generating bubbles in a liquid, and thereby generating plasma in the bubbles.

A sheet-like chip 202 made of an insulation material such as polydimethyl siloxane (hereinafter referred to as PDMS), in which a narrow portion 103 is patterned is mounted on a quartz glass 201. The chip 202 is produced by patterning into a flow channel pattern of a resist material using photolithography. When the chip 202 is mounted on the quartz glass 201, the chip eventually adheres to the glass to form a microflow channel. In the chip 202, solution reservoirs 102 are formed by perforating a hole at a portion corresponding to the end of the flow channel 101 with a perforating equipment such as a punch.

Through various tries on the planar shape of the flow channel 101, the conditions for the most stable plasma are earnestly desired. The height of the flow channel 101 in a direction perpendicular to the plane shown in FIG. 2 is about 70 μm.

As the conductive liquid 105, a phosphate buffer under physiological conditions, which is frequently used in biological fields, diluted to 1/20 (a volume ratio) was used. As electrodes 104, a platinum wire having a diameter of 0.5 mm was used. When a voltage of 300 to 1500 V was applied to the electrodes 104, plasma 106 was generated in the narrow portion 103. The emission spectroscopic analysis could be performed by introducing light 203 from the plasma 106 into optical fibers 204, and determining the spectrum with a spectrometer manufactured by Ocean Optics Inc. (the product number: USB2000).

Example 3

FIG. 3 and FIG. 4 are plan views of a flow channel pattern 1 and flow channel pattern 2, respectively. Each of these flow channel patterns was used when a flow channel pattern capable of generating stable plasma was studied. In FIG. 3 and FIG. 4, the solid-white portions show flow channel patterns and the circular portions on the left and right sides show the shapes of the reservoirs. The central distance between the reservoirs is 6 mm. A total of 24 kinds of the flow channel patterns were studied. As a result, the flow channel pattern in which plasma is most stably generated is shown in FIG. 5.

FIG. 5 is a schematic plan view of the flow channel pattern. In FIG. 5, the width of the reservoir is 3 mm, and the distance between an end portion of the reservoir and an end portion of the reservoir is 3 mm. Also, the narrow portion has a length of 1 mm and a width of 100 μm. In the narrow portion, a semicircular projection portion having a radius of 50 µm is provided so as to have a central distance of 0.23 mm.

The flow channel pattern shown in FIG. 5 was used, and as the conductive liquid, a phosphate buffer diluted in a volume ratio of 1/20 was used (liquid temperature: 25° C.). As the electrodes, a platinum wire was used, and a voltage of 700 V was applied between the electrodes, thereby generating an electric field. At that time, the electric current was about 400 µA. Plasma was only generated in the narrow portion but not in the surrounding of the platinum electrodes. The plasma was continuously generated for 10 seconds, a period of which the electric field was applied. A photograph of the microplasma generated at that time is shown in FIG. 6. In FIG. 6, the bright portion of the narrow portion shows the generated plasma.

Next, the emission spectrum obtained from the plasma shown in FIG. 6 was examined. The results are shown in FIG. 7.

As shown in FIG. 7, only a sharp peak from sodium atom was found at a wavelength of 589 nm, and peaks from other atoms were very small. In addition, when the detection limit was estimated from the intensity of this peak and the concentration of sodium contained in the conductive liquid, the detection limit was found to be about 10 ppm in this system. This detection limit is ascribed to the noise level of the spectrometer used and is not intended to mean an essential detection limit in the method for generating plasma of the present invention. The essential detection limit in the method for generating plasma of the present invention is considered to be far smaller than this value.

Example 4

The same procedures as in Example 3 were carried out except that an aqueous potassium chloride (liquid temperature: 25° C.) at a concentration of 0.01 mol/liter (hereinafter referred to as M) was used in place of the phosphate buffer in Example 3, to examine the emission spectrum. The results are shown in FIG. 8.

From the measurement results of the emission spectrum shown in FIG. 8, besides sharp peaks from potassium atom at wavelengths of 766 nm and 770 nm, a peak from sodium atom at a wavelength of 589 nm was found. The peak from sodium atom is ascribed to the emission from the sodium atom adhered in the flow channel during the experiment using the phosphate buffer immediately preceding thereof, showing that the cleaning in the system was unsatisfactory. Especially, it is well known that sodium is difficult to clean even in an experiment of flame reaction or the like. Therefore, the results are reasonable even though emission takes place from the remainder of cleaning in this experiment, which is not considered to be essential disadvantage. In addition, it can be seen from the results shown in FIG. 8 that the peaks from other atoms are very small.

Next, the detection limit was estimated from the intensity of this peak and the concentration of sodium contained in the conductive liquid. As a result, the detection limit in this system was about 5 ppm. This limit is ascribed to the noise level of the spectrometer used, and the essential detection limit in the method for generating plasma of the present invention is considered to be far smaller than this value.

Example 5

The flow channel pattern shown in FIG. 5 was used, and as the conductive liquid, a 0.1 M aqueous sodium chloride (liquid temperature: 25° C.) was used.

As electrodes, a platinum wire having a diameter of 0.5 mm was used. The electrodes were immersed in the above-mentioned aqueous sodium chloride. The variance in the emission intensity of the sodium atom from generated plasma in the case where a voltage of 500 V was continuously applied to the electrodes, and the variance in the emission intensity of the sodium atom from generated plasma in the case where a voltage of 500 V was applied to the electrodes with a pulse for a time period of 250 ms were examined. The results are shown in FIG. 9. In FIG. 9, the graph plotted with squares shows variance in emission intensity when voltage is applied with a pulse for a time period of 250 ms; and the graph plotted with circles shows variance in emission intensity when voltage is continuously applied.

As is evident from the results shown in FIG. 9, it can be seen that the variance in emission intensity obtained is large in the case where an electric field is continuously applied, as compared to the case where an electric field is applied with pulse. This is because when an electric field is continuously applied, the generated plasma develops to a size larger than the volume of the narrowed portion of the flow channel, thereby resulting in dramatic change in the shape and brightness of the plasma. On the other hand, when an electric field is applied in the form of a pulse, the emission is terminated before the plasma develops to a large size and unstable, so that the emission intensity can be measured only with the emission from the plasma that is always in the same state.

It can be seen from the above that the method of applying an electric field with a pulse leads to stabilization of the temperature of the plasma, which is very useful in quantification of atoms contained in the conductive liquid.

Here, a pulse width effective for stabilization of the plasma, in other words, the time period for applying an electric field is preferably 500 ms or less, more preferably from 1 µs to 500 ms, even more preferably from 1 µs to 100 ms, and even more preferably from 1 to 100 ms, in single application.

Example 6

The flow channel pattern shown in FIG. 5 was used, and as the conductive liquid, a 0.01 M aqueous sodium chloride, a 0.05 M aqueous sodium chloride, or a 0.1 M aqueous sodium chloride (each liquid temperature: 25° C.) was used.

As electrodes, a platinum wire having a diameter of 0.5 mm was used. The electrodes were immersed in the above-mentioned aqueous sodium chloride, and each of the electric fields listed in Tables 1 to 3 was applied with a pulse width of 20 ms, 50 ms, 100 ms, 200 ms, or 500 ms to examine the generation of plasma. The results are shown in Tables 1 to 3.

Table 1 shows the results when a 0.01 M aqueous sodium chloride was used, and the electroconductivity was 1.09 mS/cm. Table 2 shows the results when a 0.05 M aqueous sodium chloride was used, and the electroconductivity was 4.9 mS/cm. Table 3 shows the results when a 0.1 M aqueous sodium chloride was used, and the electroconductivity was 8.6 mS/cm.

In addition, in each table, ○ shows that plasma is generated, and X shows that plasma is not generated.

TABLE 1

Presence or Absence of Generation of Plasma at Each Pulse Width

| Voltage (V) | Pulse Width (ms) | | | | |
|---|---|---|---|---|---|
| | 20 | 50 | 100 | 200 | 500 |
| 200 | X | X | X | X | X |
| 250 | X | X | X | X | X |
| 300 | X | X | X | X | X |
| 350 | X | X | X | X | X |
| 400 | X | X | X | X | O |
| 450 | X | X | X | X | O |
| 500 | X | X | X | X | O |
| 600 | X | X | O | X | O |
| 700 | O | X | O | O | O |
| 800 | O | X | O | O | O |
| 900 | O | O | O | O | O |
| 1000 | O | O | O | O | O |

TABLE 2

Presence or Absence of Generation of Plasma at Each Pulse Width

| Voltage (V) | Pulse Width (ms) | | | | |
|---|---|---|---|---|---|
| | 20 | 50 | 100 | 200 | 500 |
| 200 | X | X | X | X | X |
| 250 | X | X | X | X | X |
| 300 | X | X | X | X | X |
| 350 | X | X | X | X | X |
| 400 | X | X | X | X | O |
| 450 | X | X | X | O | O |
| 500 | X | X | O | O | O |
| 600 | O | X | O | O | O |
| 700 | O | O | O | O | O |
| 800 | O | O | O | O | O |
| 900 | O | O | O | O | O |
| 1000 | O | O | O | O | O |

TABLE 3

Presence or Absence of Generation of Plasma at Each Pulse Width

| Voltage (V) | Pulse Width (ms) | | | | |
|---|---|---|---|---|---|
| | 20 | 50 | 100 | 200 | 500 |
| 200 | X | X | X | X | X |
| 250 | X | X | X | X | X |
| 300 | X | X | X | X | O |
| 350 | X | X | X | O | O |
| 400 | O | O | O | O | O |
| 450 | O | O | O | O | O |
| 500 | O | O | O | O | O |
| 600 | O | O | O | O | O |
| 700 | O | O | O | O | O |
| 800 | O | O | O | O | O |
| 900 | O | O | O | O | O |
| 1000 | O | O | O | O | O |

As is clear from the results shown in Tables 1 to 3, the conditions for generating plasma depend upon the electroconductivity of the conductive liquid. It is considered that as the conditions for generating plasma change, the plasma temperature or the like also differs, and that different emission intensities are given to samples having the same concentration of the measured element. Therefore, for measurement having high precision of samples having different electroconductivities, it is necessary to adjust the conditions for generating plasma such as intensity of electric field in each measurement, to draw calibration curves for different electroconductivities in each measurement, or to perform both.

In addition, since the majority of the anticipated samples (conductive liquid) have a very low concentration of electrolytes, a large electric field is required for the generation of plasma.

Here, the electroconductivity can be adjusted to be higher by previously adding an electrolyte that does not hinder the measurement of the sample. Therefore, a highly precise measurement can be made by adjusting the electroconductivity of the sample to a level that is convenient to the generation and measurement of plasma. Furthermore, by the adjustment of the electroconductivity, the electroconductivity of the sample is adjusted so as to have the same level of electroconductivity for each time, whereby the conditions for generating plasma such as electric field during measurement can be set to be nearly in the same level. By having the conditions set to be nearly in the same level, the designing of a measurement apparatus becomes simpler, the adjustment of the conditions for generating plasma becomes simpler, and the reproducibility and measurement precision also become higher. The above-mentioned electrolyte that does not hinder the measurement refers to an electrolyte which is only composed of elements of different kinds from the elements to be measured, the electrolyte that does not hinder the measurement of the element intended to be measured, such as an electrolyte that does not form any precipitate due to a particular reaction with the sample, or an electrolyte has a wavelength that does not overlap with the wavelength of the elements to be measured during the measurement of emission spectrum.

For example, the electroconductivity that is convenient to the generation and measurement of plasma is 8.6 mS/cm. When a sample having an electroconductivity of this value or less is used, sodium and chlorine are not included in the elements to be measured, and sodium and chlorine do not particularly hinder the measurement, sodium chloride is added to the sample, so that the electroconductivity of the sample can be adjusted to 8.6 mS/cm, whereby high-precision quantitative measurement can be easily performed each time under nearly the same conditions for generating plasma.

The majority of the samples are expected to have an electroconductivity smaller than the value convenient to the generation and measurement of plasma by two digits. In that case, the electroconductivity can be adjusted by simply adding a given amount of the electrolyte to a given amount sample each time, without particularly measuring the electroconductivity or the concentration of the sample.

When the sodium concentration or the chlorine concentration in the sample is measured, it is necessary to use an electrolyte that does not contain these elements. As the electrolyte, nitric acid is preferable because nitric acid is capable of melting a number of metals and does not contain elements other than those contained in air, water, or the like.

Example 7

The intensity of the emission to the concentration of the solution was examined (each liquid temperature: 25° C.) using plasma that was generated in the same manner as in Example 6 and using as conductive liquids a 0.01 M aqueous potassium chloride, a 0.05 M aqueous potassium chloride, or a 0.1 M aqueous potassium chloride. The results are shown in FIG. 10. FIG. 10 is graphs showing calibration curves and variance when plasma is generated.

Each of the conductive liquids contains a 0.1 M sodium chloride, an applied voltage is 500 V, and a pulse width is 250 ms.

FIG. 10(a) shows a calibration curve of which ordinates are emission intensity (K intensity) of potassium, wherein the calibration curve is obtained by generating three pulses during one measurement, assuming an average of the emission intensity as a measurement datum for one run, and obtaining a curve from 10 measurement data for each concentration.

As shown in FIG. 10(a), an about 50% variance is found in the calibration curve. The variance is considered to be caused by the change in the relationship between the position at which plasma is generated and the position of the optical fiber, variance in the voltage and the time period of applying voltage on the pulse power source, variance in the conditions for generating plasma, or the like. Some of these variances can be corrected to some extent by previously mixing a sample and an additional element which is not in elements to be measured and has a known concentration, and taking a ratio of the emission intensity using the emission intensity of the element having a known concentration as a standard. Sodium chloride or the like added for adjusting electroconductivity can be utilized for this purpose.

FIG. 10(b), as described above, shows a calibration curve, in which values of a ratio obtained by dividing the emission intensity of potassium the emission intensity of sodium measured at the same time (K/Na intensity) are used as the ordinate, wherein in the same manner as above, the calibration curve is obtained by generating three pulses during one measurement, assuming an average of the emission intensity as one measurement datum, and obtaining a curve from 10 measurement data for each concentration.

As shown in FIG. 10(b), variance in the calibration curve was within 5%. Further, the measurement was taken in the same manner by allowing the sample (conductive liquid) to migrate during the three pulses, and allowing a fresh sample to always flow into a portion at which plasma is generated. As a result, the variance was within 1%. It can be seen from this fact that when an electric field is applied multiple times, and the conductive liquid is allowed to migrate after applying the electric field and during application of a subsequent electric field, the occurrence of variance in the emission intensity can be suppressed.

Example 8

One embodiment of the apparatus for emission spectroscopic analysis in which the apparatus for generating plasma of the present invention is used is shown in FIG. 11. The apparatus shown in FIG. 11 is an apparatus for emission spectroscopic analysis capable of detecting plasma emission using a photosensor to control electricity supply.

A chip 202 is made of an insulation material. In a flow channel 101, a narrow portion 103 having a cross-sectional area significantly smaller than a cross-sectional area of the flow channel is provided. Electrodes 104 are inserted in the flow channel as a means of applying an electric field to the narrow portion 103 so as to allow the electric field to conduct through the narrow portion 103, and the electrodes 104 are connected to the power source 301.

The light emitted from plasma is captured by a photosensor (not illustrated in the figure) which is built-in a photosensor unit 302 arranged in the lower portion of the chip 202. The photosensor unit 302 is capable of controlling the connection and disconnection of the electric field with a switch 303 on the basis of the emission intensity captured with the photosensor, and stopping the application of the electric field after a designated period of time from the generation of plasma, whereby emission intensity, emission time, and the number of emission can be controlled.

A photoreceptive unit comprises a reflective plate such as a mirror, so that the amount of condensation of light may be increased in the photoreceptive unit. Also, a condensing lens may be provided between an emission point and a photoreceptive point, whereby condensation of light can be efficiently carried out.

When this apparatus is used, emission intensity, emission time, and emission frequency can be controlled by capturing light emitted from plasma with a photosensor; and recognizing that plasma is generated at a point where the emission intensity reaches a given level or higher, and stopping application of an electric field after a designated period of time from the generation of plasma.

When the application of the electric field is continued, intermittent emission is carried out. This emission is affected by bubbles generated in the narrow portion or surroundings thereof, so that a position at which the plasma is generated is less likely to be stable, and at the same time the size of plasma is also less likely to be stable. Therefore, as shown in FIG. 11, the electric field is controlled, with the generation of plasma, whereby the position at which the plasma is generated and the size of the plasma can be stabilized.

Example 9

The flow channel pattern shown in FIG. 5 was used, and as the conductive liquid, a 0.1 M aqueous sodium chloride (liquid temperature: 25° C.) was used. As electrodes, a platinum wire having a diameter of 0.5 mm was used. The electrodes were immersed in the above-mentioned aqueous sodium chloride and a voltage of 500 V was continuously applied to the electrodes.

FIG. 12 shows a time transition of the emission intensity during the plasma emission. FIG. 12(a) is a graph showing a time transition of the emission intensity. FIG. 12(b) is a graph showing an emission spectrum in the time zone I in FIG. 12(a). FIG. 12(c) is a graph showing an emission spectrum in the time zone II in FIG. 12(a).

It can be seen from the results shown in FIG. 12 that it can be from the comparison of single plasma emission by dividing into time zones that the characteristics of the spectra that differ depending upon the time zones from the beginning of the emission can be grasped. Therefore, by using the data of time zone in which a wavelength intended to be measured is a peak, the emission spectrum can be measured in high sensitivity. In addition, when the difference from one of other time zones is obtained, the influence by the background can be eliminated, and whereby the measurement of the emission spectrum in a higher sensitivity can be accomplished.

INDUSTRIAL APPLICABILITY

According to the present invention, in order to analyze elements contained in solution, a solution is introduced into plasma, whereby identification and quantification of the elements contained in the solution can be performed by the emission spectrum from the elements therein. Therefore, each of the method for generating plasma, the method for emission spectroscopic analysis, and the apparatus for generating plasma, and the apparatus for emission spectroscopic analysis comprising the apparatus for generating plasma can be suitably used in the field of microfluid mechanism or in the field called μTAS or lab-on-a-chip.

The invention claimed is:

1. A method for generating plasma comprising the steps of providing a narrow portion in a flow channel made of an insulation material, the narrow portion having a cross-sectional area markedly smaller than a cross-sectional area of the flow channel, wherein the flow channel has a thickness of from 2 μm to 30 mm and has a width of from 2 μm to 30 mm, and wherein the narrow portion has a thickness of from 0.5 μm to 1 mm and has a width of from 0.5 μm to 1 mm, and wherein the flow channel comprises the narrow portion having a cross-sectional area markedly smaller than a cross-sectional area of the flow channel;

filling the flow channel and the narrow portion with a conductive liquid, and thereafter applying an electric field to the narrow portion to form bubbles at the narrow portion, to conduct the electric field through said narrow portion, wherein the length of the direction of the electric field at the narrow portion is from 2 μm to 3 mm, thereby generating plasma in the formed bubbles at said narrow portion.

2. The method for generating plasma according to claim 1, wherein a ratio of the cross-sectional area of the flow channel to the cross-sectional area of the narrow portion (the cross-sectional area of the flow channel/the cross-sectional area of the narrow portion) is 3 or more.

3. The method for generating plasma according to claim 1, wherein the time period for applying an electric field is from 1 μs to 500 ms in single application of the electric field.

4. The method for generating plasma according to claim 1, wherein in a case where electric field is applied plural times, the conductive liquid is migrated after the application of the electric field and before the subsequent application of the electric field.

5. The method for generating plasma according to claim 1, wherein the electric field is applied from a pair of electrodes arranged in the flow channel in a manner that the narrow portion is sandwiched therewith.

6. A method for elemental analysis comprising the steps of providing a narrow portion in a flow channel made of an insulation material, the narrow portion having a cross-sectional area markedly smaller than a cross-sectional area of the flow channel, wherein the flow channel has a thickness of from 2 μm to 30 mm and has a width of from 2 μm to 30 mm, and wherein the narrow portion has a thickness of from 0.5 μm to 1 mm and has a width of from 0.5 μm to 1 mm, and wherein the flow channel comprises the narrow portion having a cross-sectional area markedly smaller than a cross-sectional area of the flow channel;

filling the flow channel and the narrow portion with a conductive liquid for identification or quantification of elements, and thereafter applying an electric field to the narrow portion to form bubbles at the narrow portion, to conduct the electric field through said narrow portion, wherein the length of the direction of the electric field at the narrow portion is from 2 μm to 3 mm, thereby generating plasma in the formed bubbles at said narrow portion; and subjecting light from the generated plasma to spectroscopy.

7. The method for elemental analysis according to claim 6, wherein a ratio of the cross-sectional area of the flow channel to the cross-sectional area of the narrow portion (the cross-sectional area of the flow channel/the cross-sectional area of the narrow portion) is 3 or more.

8. The method for elemental analysis according to claim 6, wherein the time period for applying an electric field is from 1 μs to 500 ms in single application of the electric field.

9. The method for elemental analysis according to claim 6, wherein in a case where electric field is applied plural times, the conductive liquid is migrated after the application of the electric field and before the subsequent application of the electric field.

10. The method for elemental analysis according to claim 6, wherein a given electrolyte is previously added to the conductive liquid to adjust electroconductivity of the conductive liquid.

11. The method for elemental analysis according to claim 6, wherein the electric field is applied from a pair of electrodes arranged in the flow channel in a manner that the narrow portion is sandwiched therewith.

12. An apparatus for generating plasma in a conductive liquid, the apparatus for generating plasma comprising a narrow portion in a flow channel made of an insulation material, the narrow portion having a cross-sectional area markedly smaller than a cross-sectional area of the flow channel, wherein the flow channel has a thickness of from 2 μm to 30 mm and has a width of from 2 μm to 30 mm, and wherein the narrow portion has a thickness of from 0.5 μm to 1 mm and has a width of from 0.5 μm to 1 mm, and wherein the flow channel comprises the narrow portion having a cross-sectional area markedly smaller than a cross-sectional area of the flow channel; and a means of applying an electric field to the narrow portion to conduct the electric field through the narrow portion.

13. The apparatus for generating plasma according to claim 12, wherein the apparatus comprises a pair of electrodes arranged in the flow channel in a manner that the narrow portion is sandwiched therewith.

14. The apparatus for generating plasma according to claim 12, wherein a ratio of the cross-sectional area of the flow channel to the cross-sectional area of the narrow portion (the cross-sectional area of the flow channel/the cross-sectional area of the narrow portion) is 3 or more.

15. The apparatus for generating plasma according to claim 12, wherein the narrow portion is detachably arranged.

16. An apparatus for emission spectroscopic analysis comprising the apparatus for generating plasma as defined in claim 12.

* * * * *